United States Patent [19]

Congy et al.

[11] Patent Number: 5,166,416

[45] Date of Patent: Nov. 24, 1992

[54] PROPENONE OXIME ETHERS, A METHOD OF PREPARING THEM, AND PHARMACEUTICAL COMPOSITIONS CONTAINING THEM

[75] Inventors: Christian Congy, Saint-Gely-Du-Fesc; Patrick Gueule, Teyran; Bernard Labeeuw, Montpellier; Murielle Rinaldi, St. Georges d'Orques, all of France

[73] Assignee: Societe Anonyme: Sanofi, Paris, France

[21] Appl. No.: 444,823

[22] Filed: Dec. 1, 1989

[30] Foreign Application Priority Data

Dec. 2, 1988 [FR] France ............................ 88 15860

[51] Int. Cl.$^5$ ................. C07C 121/78; C07C 131/00
[52] U.S. Cl. ............................. 562/114; 562/595; 562/597; 544/124; 544/146; 544/364; 546/192; 546/193; 546/212; 546/214; 546/281; 546/338; 549/59; 549/472; 549/75; 564/256
[58] Field of Search ............ 549/59, 75, 472; 562/114, 595, 597; 564/256; 546/338, 192, 193, 212, 214, 281; 544/124, 146, 364

[56] References Cited

U.S. PATENT DOCUMENTS 4,081,552  3/1978  Welle et al. ............... 562/595 X
4,085,225  4/1978  Welle et al. ............... 562/595 X
4,086,361  4/1978  Welle et al. ............... 562/595 X

FOREIGN PATENT DOCUMENTS 0017217  10/1980  European Pat. Off. .

*Primary Examiner*—Arthur C. Prescott
*Assistant Examiner*—V. Garner
*Attorney, Agent, or Firm*—Bacon & Thomas

[57] ABSTRACT

The invention relates to new propenone oxime ethers, a method of preparing them and pharmaceutical compositions containing them.

Said new propenone oxime ethers have the formula $$Ar'-C-C=C-Ar \atop \underset{N}{\|} \underset{M}{\phantom{|}} \underset{O-(CH_2)_n-N<^{R_1}_{R_2}}{\phantom{|}} \quad (I)$$

in which—Ar and Ar' each independentlyl denotes a phenyl group non-substituted, mono or polysubstituted, a 9-anthryl group or a naphthyl group, a pyridyl, thienyl or furyl group;

$R_1$ $R_2$ each independently denotes hydrogen, a $C_1$–$C_4$ alkyl group or together with the N-atom to which they are bonded a 1-pyrrolidinyl, piperidino, morpholino or 1-piperazinyl group;

M=H, Cl, Br or a $C_1$–$C_6$ alkyl group n=2 or 3.

The invention also deals with the salts of compounds of formula (I). Said compounds have good activity in the anti platelet-clotting tests and are also antagonists of the $5HT_2$ receptors.

15 Claims, No Drawings

PROPENONE OXIME ETHERS, A METHOD OF PREPARING THEM, AND PHARMACEUTICAL COMPOSITIONS CONTAINING THEM

The invention relates to novel 2-propene 1-one 0-substituted oxime ether compounds comprising various aromatic and heteroaromatic rings in positions 1 and 3. It also deals with a method of preparing them and pharmaceutical compositions containing them. The compounds according to the invention have interesting therapeutic properties.

More particularly the compounds have an effect on the central and peripheral nervous system and are antagonists of the $5HT_2$ receptors.

Numerous biological processes (appetite, sleep, sexual activity, depression, mood, arterial hypertension) are partly connected with the action of a neurotransmitter, i.e. serotonin or 5-hydroxy tryptamine or 5HT (R. Glennon, Journal of Medicinal Chemistry, 1987, 30, 1).

Their effects are due to interaction of the product with specific bonding sites (5HT receptors) present at the central and peripheral level (gastro-intestinal tract, lungs, cardiovascular system). At present three types of sites: $5HT_1$, $5HT_2$ and $5HT_3$—have been described, with sub-types. It appears that type $5HT_2$ receptors occur in certain cerebral syndromes and may play a part in clotting of platelets (F. DE CLERK et al., Biochemical Pharmacology, 1984, 33, 2807), arterial hypertension and migraines (G. JOHNSON, Reports in Medicinal Chemistry, 1987, 4150) and the contraction of smooth muscles (L. COHEN et al., Journal of Pharmacology and Experimental Therapeutics, 1981, 218, 421).

Diphenyl alkanol ether and diphenyl alkanone oxime ether derivatives having antispasmodic and anti blood-clotting activity and effects on cerebral insufficiency and senile dementia are described in European Patent 0 017 217.

More particularly the compound

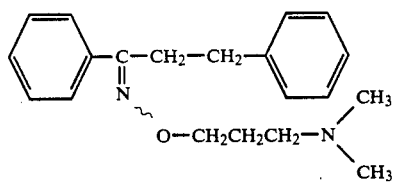

(A)

is described among products having cerebral vasodilating properties.

It has now been found that certain propenone oxime ethers are compounds having a high affinity for the $5HT_2$ receptor.

It has also been found that the aforementioned propenone oxime ethers have interesting pharmacological properties, inter alia a good anti blood-clotting effect, and are useful inter alia for treatment of any disease depending on 5HT.

According to one of its features, therefore, the invention relates to propenone oxime ethers having the formula:

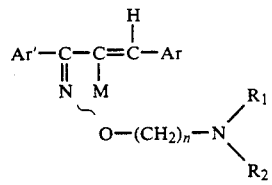

in which
Ar and Ar' can each independently denote either:
(a) a phenyl group, non-substituted or mono or polysubstituted by a halogen atom, a lower alkyl grouping (containing 1 to 4 carbon atoms), a nitro, hydroxyl, alkoxy (1–4 carbon atoms), acyloxy (1–4 carbon atoms), dimethylamino or carboxyalkoxy grouping in which the alkylene contains 1–4 carbon atoms; or a 9-anthryl group or a naphthyl group, or
(b) a heteroaromatic group chosen from among pyridyl, thienyl or furyl groups;
$R_1$ and $R_2$ each independently denote a hydrogen atom or a lower alkyl grouping (1–4 carbon atoms) or $R_1$ and $R_2$ together with the nitrogen atom to which they are bonded constitute a 1-pyrrolidinyl or piperidino or morpholino or 1-piperazinyl grouping;
M represents a hydrogen atom or a chlorine or bromine atom, or a straight or branched lower alkyl containing 1–6 carbon atoms, and
$n = 2$ or 3,
and their salts with mineral or organic acids.

Among the heteroaromatic groups, 3-pyridyl, 2-thienyl, 3-thienyl or 2-furyl are preferred groups.

The mineral or organic acids which form the addition salts according to the invention comprise acids of use for suitable separation or crystallization of formula I compounds, e.g. picric acid or oxalic acid, or acids for forming pharmaceutically acceptable salts such as the hydrochloride, hydrobromide, sulphate, hydrogen sulphate, dihydrogen phosphate, methane sulphonate, methyl sulphate, maleate, fumarate, naphthalene sulphonate or isethionate.

As is known, compounds having the formula

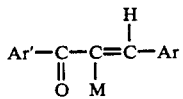

where Ar and Ar' have the previously-given meanings, such compounds being called "chalcones", occur preferentially in the trans form with respect to the propene double bond (Bull. Soc. Chim. France, 1961, 5, 1369).

The compounds (I) according to the invention are oximes of chalcones and have a trans geometry with respect to the carbon-carbon double bond.

With regard to the geometry of the C=N bond of the O-substituted oxime, the formula

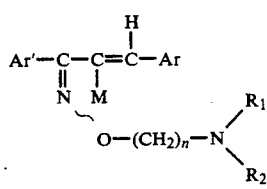

indicates that the substance is a mixture in various proportions of the syn(s) and anti(a) isomers, which are represented as follows (J. Chem. Soc., 1981, 860):

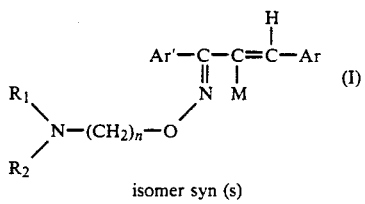

isomer syn (s)

and

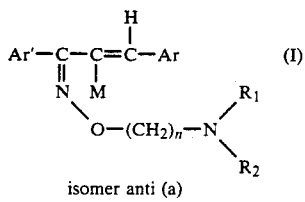

isomer anti (a)

In a preferred embodiment, the invention relates more particularly to a propenone oxime ether according to (I), having the formula:

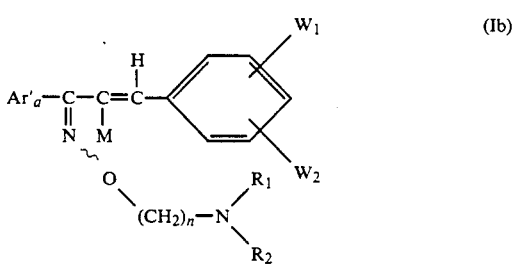

where $Ar'_a$ represents an aromatic group chosen from among pyridyl, thienyl, furyl or 9-anthryl and $W_1$ and $W_2$ each independently represent a hydrogen atom or a halogen atom or a lower alkyl grouping (1-4 carbon atoms) or a nitro or hydroxyl or alkoxy (1-4 carbon atoms) or acyloxy (1-4 carbon atoms) or dimethylamino or carboxyalkoxy group in which the alkylene contains 1 to 4 carbon atoms, or a salt thereof with mineral or organic acids.

According to another embodiment, the invention relates more particularly to a propenone oxime ether according to (I), having the formula:

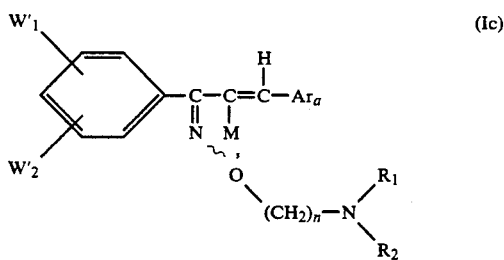

in which $Ar_a$ represents a group chosen from among pyridyl, thienyl, furyl or 9-anthryl and $W'_1$ and $W'_2$ each independently represent a hydrogen atom or a halogen atom or a lower alkyl grouping (1 to 4 carbon atoms) or a nitro, hydroxyl, alkoxy (1 to 4 carbon atoms) acyloxy (1 to 4 carbon atoms), dimethylamino or carboxyalkoxy group in which the alkylene contains 1 to 4 carbon atoms, or a salt thereof with mineral or organic acids.

Other preferred compounds according to the invention have the formula:

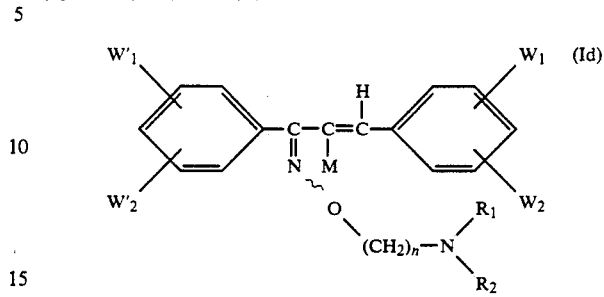

in which $W_1$, $W_2$, $W'_1$, $W'_2$ can independently denote a hydrogen atom or a halogen atom or a lower alkyl grouping (1-4 carbon atoms) or a nitro or hydroxyl or alkoxyl (1-4 carbon atoms) or acyloxy (1-4 carbon atoms) or dimethylamino or carboxyalkoxy group in which the alkylene contains 1 to 4 carbon atoms;

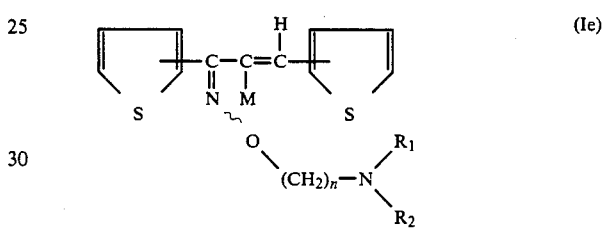

in which the substituents are a 2-thienyl or a 3-thienyl.

The compounds are in base or salt form with mineral or organic acids.

According to another feature, the invention relates to a method of preparing formula (I) compounds and salts thereof, characterised in that a) a chalcone having the formula:

is treated with a hydroxylamine having the formula:

$$H_2NOZ \quad (III)$$

in which Z represents either
an aminoalkyl chain having the formula:

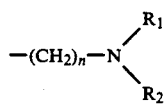

where $R_1$ and $R_2$ have the meanings described for (I), or
a hydrogen atom or
a substituted alkyl group having the formula:

$$-(CH_2)_nX$$

where X represents a leaving group; and in that
b) the resulting product having the formula:

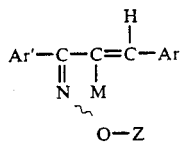
(Ia)

where Ar and Ar' are as defined hereinbefore and where Z represents hydrogen or the —(CH$_2$)$_n$X group is then, when Z is hydrogen and in the presence of a basic condensation agent, treated either with an amine having the formula:

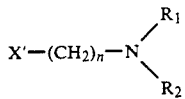
(V)

in which R$_1$ and R$_2$ are as defined hereinbefore and X' is a leaving group or, when Z represents a group

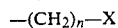

where X is as defined hereinbefore, the resulting product is treated with an amine having the formula:

where R$_1$ and R$_2$ are as defined hereinbefore, and in that c) the product thus obtained in (a) or (b) is converted if necessary into one of its salts.

The leaving groups represented by X and X' can be one of the substituents generally used for preparing alkylamines, e.g. a halogen atom or a hydroxysilyl or hydroxy group esterified with methanesulphonic acid.

The following reaction diagram indicates the method of preparing the compounds according to the invention:

The choice of the method of synthesis will depend on the availability of the various hydroxylamines and the method of preparation thereof.

Salts of hydroxylamines O-substituted by an alkylamino chain having the formula:

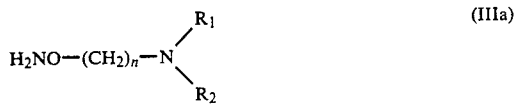
(IIIa)

can be prepared by methods described in the literature (Chimia, 1964, part 1, 18, 1, 36) and can yield the compounds I according to the invention in a single reaction with chalcones (II) in a solvent such as reflux-heated ethanol.

The hydroxylamine salt condensed on to a chalcone (II) in alcohol or pyridine yields the oxime having the formula:

(Ia')

which is then treated in a first step with a base such as sodium hydride or potassium carbonate in a polar aprotic solvent such as dimethyl formamide, dimethyl acetamide or dimethyl sulphoxide, and is then substituted by an alkylamine (V) comprising a leaving grouping X' having the formula:

(V)

yielding the compounds (I) according to the invention.

In another variant of the general method of synthesis, a chalcone (II) is reacted in an alkanol at ambient temperature with an O-alkylated hydroxylamine salt, for example hydrochloride having the formula:

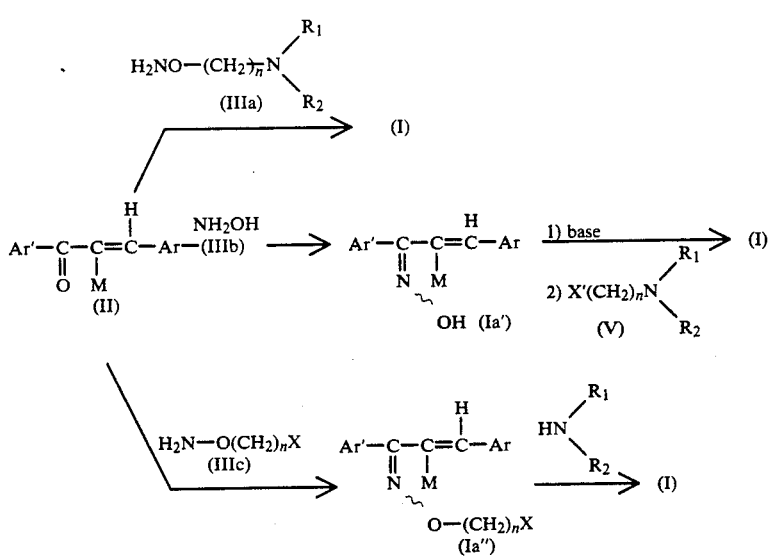

HCl,H₂N—O(CH₂)ₙX     (IIIc)

comprising a starting grouping X, so as to obtain the intermediate having the formula:

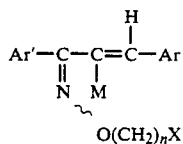     (Ia'')

which is then substituted by an amine, either in a solvent such as water or dimethyl formamide or in the absence of a solvent and in the presence only of the amine, thus finally yielding the compounds (I) according to the invention.

After thus being obtained, the formula (I) product is isolated in the form of the free base or salt, by conventional methods.

When the formula (I) compound is obtained in the form of the free base, it is converted into a salt by treatment with the chosen acid in an organic solvent. The free base, dissolved e.g. in an alcohol such as isopropanol, is treated with a solution of the chosen acid in the same solvent, thus obtaining the corresponding salt, which is isolated by conventional techniques. This method is used e.g. for preparing the hydrochloride, hydrobromide, sulphate, hydrogen sulphate, dihydrogen phosphate, methane sulphonate, methyl sulphate, oxylate, maleate, fumarate, 2-naphthalene sulphonate and isethionate.

At the end of the reaction between compound (II) and compound (III), the formula (I) compound can be isolated in the form of one of its salts, e.g. the hydrochloride or the oxalate. In that case, if necessary, the free base can be prepared by neutralizing the salt with a mineral or organic base such as sodium hydroxide or triethylamine or an alkali-metal carbonate or bicarbonate such as sodium or potassium carbonate or bicarbonate, and can then if required be converted into another of its salts.

The configuration of an isomer and the relative proportions of a mixture of syn and anti isomers are determined by NMR.

The syn and anti isomers in a mixture are separated by crystallization of salts such as oxalates, maleates, fumarates and hydrochlorides of compounds having the formula (I).

The chalcones (II) are known or prepared by methods described in the literature (Houben Weyl 10-1, 1181) by Claisen-Schmidt condensation, by reacting an aldehyde Ar—CHO with a ketone Ar'—CO—Alk (Alk represents an alkyl containing 1 to 7 carbon atoms).

Carrying out the process of the invention, novel derivatives of 2-propene 1-one of formula (II) may be used. Such novel derivatives—key intermediates—constitute another subject of the invention, more particulary those of formula:

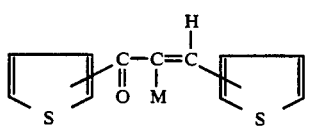

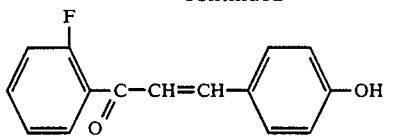

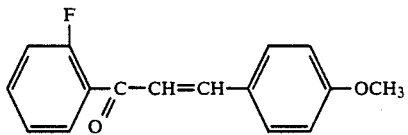

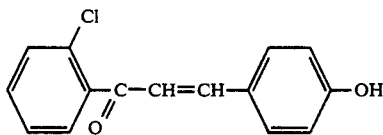

Such derivatives are prepared by known methods. For example, the one bearing a thiophenic derivative may be prepared by substitution of a 3-thiophene carboxaldehyde with a 3-acetyl thiophene.

The compounds according to the invention have been subjected to biological and pharmacological tests and compared with the prior-art compound (A).

The compounds (I) have good activity in the anti platelet-clotting test after T. HALLAM et al. Thrombosis Research 1982, 27, 435–445. The 50 inhibiting concentration of the most active compounds is 5 to 50 times as small as that of compound (A).

Also, compounds (I) have high affinity in vitro and in vivo for 5HT₂ receptors.

These tests are carried out under the experimental conditions described by J. LEYSEN et al., Molecular Pharmacology, 1982, 21, 301–314 as regards the tests in vitro and as per J. FROST et al., Life Sciences, 1987, 40, 987–997 as regards the tests in vivo.

Stimulation of a rabbit's abdominal aorta strip shows activity 50 to 1500 times as great as that of product (A), with regard to antagonism to peripheral 5HT receptors. The tests were made after E. APPERLEY et al., Br. J. of Pharmacol., 1976, 58, 211–221.

The compounds according to the invention are also antagonists of the central 5HT₂ receptors. This activity was shown by the head-twitch test made after C. GOURET, J. Pharmacol., Paris, 1975, 6, 165–175.

The compounds also have an anti-convulsing activity shown by the test on antagonism to clonic spasms induced by pentetrazole (antagonism to the central 5HT₂ receptors) after P. WORMS et al., J. Pharmacol. Exp. Ther., 1982, 220, 660–670.

The formula (I) compounds have low toxicity. More particularly their acute toxicity is compatible with use thereof as drugs, e.g. to prevent clotting of platelets, or as psychotropic drugs.

For this purpose, mammals requiring this treatment are given an effective quantity of the formula (I) compound or of one of its pharmaceutically acceptable salts.

The aforementioned formula (I) compounds and their pharmaticeutically acceptable salts can be used in daily doses of 0.01 to 10 mg per kilogram body weight of the mammal under treatment, preferably at daily doses of 0.1 to 5 mg/kg. In man, the dose can preferably vary from 0.5 to 500 mg per day, more particularly from 2.5 to 250 mg depending on the patient's age or the type of treatment, i.e. whether prophylactic or curative.

The formula (I) compounds are generally administered in unit doses. The unit doses are preferably formulated in pharmaceutical compositions in which the active principle is mixed with a pharmaceutical excipient.

According to another feature, therefore, the invention relates to pharmaceutical compositions in which the active principle is an aforementioned formula (I) compound or a pharmaceutically acceptable salt thereof.

In the pharmaceutical compositions according to the invention for oral, sublingual, subcutaneous, intramuscular, intravenous, transdermic, local or rectal administration, the aforementioned formula (I) active ingredients can be administered in unit forms of administration, mixed with conventional pharmaceutical excipients, to animals and to man. The suitable unit forms of administration comprise oral forms such as tablets, capsules, powders, granules and oral solutions or suspensions, sublingual and buccal forms of administration, subcutaneous, intramuscular, intravenous, intranasal or intraocular forms of administration and rectal forms of administration.

Each unit dose can contain 0.1 to 500 mg of active ingredient, preferably 2.5 to 125 mg, in combination with a pharmaceutical excipient. Each unit dose can be administered 1 to 4 times per day.

When a solid composition is prepared in tablet form, the main active ingredient is mixed with a pharmaceutical excipient such as gelatine, starch, lactose, magnesium stearate, talc, gum arabic or the like. The tablets can be coated with saccharose or suitable other substances or treated so that they have prolonged or delayed activity and so that they continuously release a given quantity of the active principle.

A preparation in capsules is obtained by mixing the active ingredient with a diluent and pouring the resulting mixture into soft or hard capsules.

A preparation in syrup or elixir form can contain the active ingredient together with a sweetener, preferably without calories, and methyl paraben and propyl paraben antiseptics and a suitable flavouring and dye.

The powders or granules dispersible in water can contain the active ingredient mixed with dispersing agents or wetting agents or suspension agents such as polyvinyl pyrrolidone, and with sweeteners or taste adjusters.

Rectal administration is made via suppositories prepared with binders such as cocoa butter or polyethylene glycols, which melt at the rectal temperature.

Parenteral, intranasal or intraocular administration is via aqueous suspensions, or isotonic saline solutions or sterile injectable solutions containing pharmacologically compatible dispersing and/or wetting agents, e.g. propylene glycol or butylene glycol.

Alternatively the active principle can be formulated in microcapsules, with one or more excipients or additives if required.

The following examples illustrate the invention without limiting it.

The NMR spectra were recorded at 250 MHz. The positions of the signals were given in millionths with respect to trimethyl silyl propane sulphonate, and the spectra were obtained in deuterated dimethyl sulphoxide.

The coupling constants J are given in Hertz (Hz).

The following abbreviations are used:
s: singlet
d: doublet
t: triplet
m: multiplet
se: widened signal The symbol "*" in the Tables indicate that the main chemical displacements (position of singlets or of the middle of doublets, triplets or multiplets) of the compound in question are described in Table 6.

The relative proportions of syn and anti isomers (%s-%a) were determined by NMR.

The instantaneous melting-points (MP) of the recrystallized products were measured on a Kofler heating bench and are expressed in degrees Celsius.

EXAMPLE 1

Trans 1-N,N-dimethyl aminoethoxyimino 1-phenyl 3-(4-hydroxyphenyl) 2-propene; CM 40414=mixture of 20% syn isomer and 80% anti isomer.

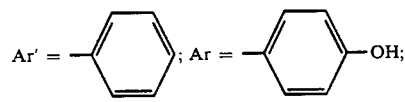

a) 4-hydroxy chalcone
Prepared as per Chemistry of Carbon Compounds, E. H. Rodd, 1956, vol. III$^B$, 1186 b) 2-N,N-dimethylamino ethoxyamine hydrochloride
Prepared as per Bull. Soc. Chim. France, 1958, 5, 664.

c) CM 40414
15 g of 4-hydroxy chalcone a) and 15 g of the compound prepared as per b) were heated with reflux and under agitation in 150 ml of absolute ethanol for 5 hours.

Concentrate the ethanol in vacuo, dissolve the residue in 200 ml of 10% acetic acid in water, wash with methylene chloride, alkalinise the aqueous phase with sodium bicarbonate, extract with methylene chloride, decant the chloromethylene phase, wash it with water, decant, dry over magnesium sulphate, filter and concentrate in vacuo. Recrystallise the residue from 500 ml ethyl acetate.

M=13 g
M.P.=175° C.

The isomer mixture contained 20% syn isomer and 80% anti isomer.

NMR spectrum

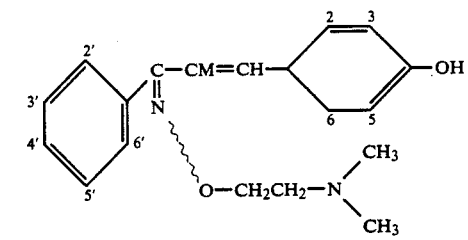

2,05 and 2,15 (6H: 1,2H syn and 4,8H anti, s, N(CH$_3$)$_2$) 2,4 and 2,55 (2H: 0,4H syn and 1,6H anti, t, J=6, CH$_2$N) 4,05 and 4,2 (2H: 0,4H syn and 1,6H anti, t, J=6, OCH$_2$) 6,2 and 6,6 (1H: 0,2H syn and 0,8H anti, d, J$_{trans}$=16, H-C=); 6,85 and 7,25 (1H: 0,2H syn and 0,8H anti, d, J$_{trans}$=16, H-C); 6,72 (2H, d, J$_{ortho}$=8, H$_{3,5}$) 7,30 (2H, d, J: 8, H$_{2,6}$) 7,40 (5H, s, H$_{2',3',4',5',6'}$).

Separation of syn and anti isomers.

d) Trans 1-N,N-dimethylaminoethoxyimino 1-phenyl 3-(4-hydroxyphenyl) 2-propene hemifumarate; anti isomer, SR 45007 A.

12.3 g of CM 40414 obtained previously were dissolved when hot in 220 ml of isopropanol and 4.6 g fumaric acid were added. Allow the solution to return to ambient temperature then leave with agitation for 1½ hours. Filter the fumarate and rinse it with ether.

M=11.6 g
M.P.=186°–187° C.

RMN spectrum 2,4 (6H, s, N(CH$_3$)$_2$) 2,85 (2H, t, J=6, N-CH$_2$) 4,25 (2H, t, J=6, OCH$_2$) 6,48 (1H, s, fumarate); 6,6 (1H, d, J$_{trans}$=16, H-C=); 6,7 (2H, d, J$_{ortho}$=8, H$_{3,5}$) 7,3 (1H, d, J$_{trans}$=16, H-C=); 7,35 (2H, d, J$_{ortho}$=8, H$_{2,6}$) 7,45 (5H, s, H$_{2',3',4',5',6'}$).

e) Trans 1-N,N-dimethylaminoethoxyimino 1-phenyl 3-(4-hydroxyphenyl) 2-propene hemifumarate, syn SR 45008 A isomer.

Concentrate the previously-obtained filtered fumarate in vacuo, dissolve residue in 50 ml acetone, separate insoluble substance by filtration then add ether until turbid and leave to crystallize. Filter the precipitate and recrystallize it from isopropanol.

M=2.0 g
M.P.=157°–159° C.

NMR spectrum 2,2 (6H, s, N(CH$_3$)$_2$) 2,7 (2H, t, J=6, NCH$_2$) 4,15 (2H, t, J=6, OCH$_2$) 6,2 (1H, d, J$_{trans}$=16, H-C=); 6,45 (1H, s, fumarate); 6,7 (2H, d, J$_{ortho}$=8, H$_{3,5}$) 6,9 (1H, d, J$_{trans}$=16, H-C=); 7,25 (2H, d, J$_{ortho}$=8, H$_{2,6}$) from 7.15 to 7.50 (5H, solid, H$_{2',3',4',5',6'}$).

Isomerization starting from the anti isomer, SR 45007 A.

In order to prepare the syn isomer, obtained in a smaller proportion during synthesis, the anti isomer was treated as follows after isolation:

17.7 g of SR 45007 A were dissolved in 200 ml absolute ethanol and 9.5 ml concentrated hydrochloric acid. Reflux-heat the reaction mixture for 6 hours then leave at ambient temperature overnight. Concentrate in vacuo, dissolve residue in water, make alkaline with sodium bicarbonate, filter the precipitate, rinse with water and dry.

m=15.1 g of a mixture of 25% syn isomer and 75% anti isomer.

The mixture was converted into a salt as per d) hereinbefore by fumaric acid to give the anti isomer, and the filtered fumarate was treated as per e) hereinbefore to obtain the syn isomer.

EXAMPLE 2

Trans 1-N,N-dimethyl aminoethoxyimino 1-phenyl 3-(4-methoxyphenyl) 2-propene oxalate: SR 45999

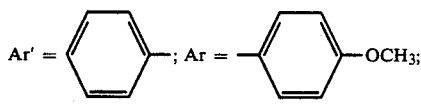

—NR$_1$R$_2$ = —N(CH$_3$)$_2$; M = H; n = 2

A mixture of 10 g 4-methoxy chalcone and 8.9 g of 2-N,N-diemthylamino ethoxyamin dihydrochloride in 150 ml absolute ethanol was reflux-heated for 7 hours.

Leave the reaction mixture to cool, filter the excess reagent and concentrate the filtrate in vacuo. Dissolve residue in water wash with ether, make the aqueous phase alkaline with a solution of concentrated ammonia, extract with ether, wash with water, dry over magnesium sulphate and concentrate in vacuo.

The yield was 12 g of an oil which was chromatographed on silica gel in order to separate the syn and anti isomers.

Eluent: methylene chloride/ethanol 97/3 (v/v)

The less polar product was eluted, yielding 6.5 g of an oil to which 1.7 g oxalic acid in 150 ml acetone were added to obtain 6.64 g of anti isomer: SR 45999 A
M.P.=162° C.

The more polar product was eluted, yielding 1.6 g of an oil to which 0.45 g oxalic acid in 20 ml acetone was added, giving 1.38 g of the syn isomer: SR 45996 A.
M.P.=179° C.

EXAMPLE 3

Trans 1-N,N-dimethylaminoethoxyimino 1-(4-methoxyphenyl) 3-(4-hydroxyphenyl) 2-propene hydrochloride

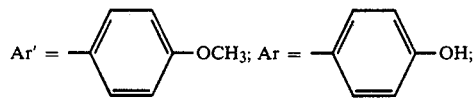

—NR$_1$R$_2$ = —N—(CH$_3$)$_2$; M = H; n = 2 a) Anti isomer: SR 45175 A

A mixture of 3 g of 4-hydroxy 4'-methoxy chalcone and 3.1 g of 2-N,N-dimethylaminoethoxyamine dihydrochloride in 50 ml ethanol was reflux-heated for 6 hours.

Leave the reaction mixture to cool, filter the crystals, agitate in 20 ml water, filter and dry to obtain 2.6 g of the anti isomer.
M.P.=216° C.

b) Mixture of 25% syn isomer and 75% anti isomer; SR 45286.

Concentrate the previously-obtained ethanolic filtrate in vacuo, dissolve residue in 100 ml water, extract twice with ethyl acetate, make alkaline at pH 8 with sodium bicarbonate, decant the aqueous phase and extract it three times with methylene chloride, wash in water, decant, dry a magnesium sulphate, and concentrate in vacuo to obtain 0.58 g of a gum which crystallises. Dissolve the crystals in 3 ml of a 70–30 (v/v) mixture of toluene and petroleum ether and filter to obtain 250 mg of a mixture of 25% syn isomer and 75% anti isomer.
M.P.=148° C.

EXAMPLE 4

Trans 1-N,N-dimethylaminoethoxyimino 1-phenyl 3-(4-acetoxyphenyl) 2-propene hemifumarate. Syn isomer: SR 46024 A

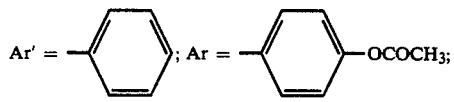

—NR$_1$R$_2$ = —N—(CH$_3$)$_2$; M = H; n = 2

1.2 g of the previously-described SR 45008 A were agitated at ambient temperature overnight in 12 ml acetic anhydride.

Concentrate the excess acetic anhydride in vacuo at 20°–30° C., add 30 ml methylene chloride, wash in water, decant the chloromethylene phase, dry over magnesium sulphate, concentrate the methylene chloride in vacuo, dissolve residue in ethyl ether, filter the precipitate and recrystallize it from ethanol, adding ether until turbid, m=0.7 g.

EXAMPLE 5

Trans 1-N,N-dimethylaminoethoxyimino di-1,3-(3-thienyl) 2-propene acid oxalate: SR 45557 A

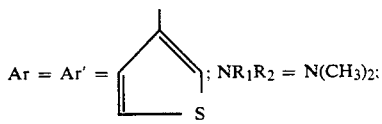

$M = H; n = 2$ a) Preparation of trans di-1,3(3-thienyl) 2-propene 1-one 2.25 g of 3-thiophene carboxaldehyde and 2.52 g of 3-acetyl thiophene were dissolved in 10 ml absolute ethanol.

A solution of 0.4 g NaOH in 1 ml water was added dropwise to the solution, cooled in ice.

The reaction mixture was agitated at 0°-5° C. for 3 hours. The precipitate was filtered, rinsed in water, dissolved in ether and dried over magnesium sulphate. The ether was concentrated in vacuo and the residue was recrystallized from cyclohexane.

M=2.8 g
M.P.=81° C.

NMR spectrum 7,58 et 7,83 (6H, m, $H_{thiophène}$, —CH=CH—); 8,08 (1H, d, $H_4$) 8,77 (1H, d, $H_{4'}$).

b) SR 45557 A

The thiophene derivative obtained as per a) was condensed with 2-N,N-dimethylaminoethoxyamine dihydrochloride as per Example 12c) hereinbefore, yielding trans 1-N,N-dimethylaminoethoxyimino 1,3 di(3-dithienyl) 2-propene, which was converted into a salt with oxalic acid, giving the acid oxalate in a mixture of 75% anti isomer and 25% syn isomer.

M.P.=138° C.

EXAMPLE 6

Trans 1-N,N-dimethylaminoethoxyimino 1-(3-thienyl) 3-(4-hydroxyphenyl) 2-propene: SR 45047.

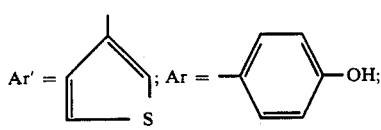

$M = H; n = 2; NR_1R_2 = N(CH_3)_2$ a) Preparation of trans 1-(3-thienyl) 3-(4-hydroxyphenyl) 2-propene 1-one 10 g 4-hydroxybenzaldehyde and 10.4 g 3-acetyl thiophene were dissolved in 40 ml of a solution of 4% hydrochloric acid in acetic acid.

Agitate the reaction mixture at ambient temperature for 4 days. Filter the precipitate, rinse with a mixture of 50% acetic acid/water then recrystallize from 30 ml ethanol. Filter the crystals.

M=8.1 g
M.P.=158° C.

NMR spectrum 6,79 (2H, d, $J_{ortho}=8$, $H_{3,5}$) 7,6 (4H, m, 2H:HC—C=et $2H_{thiophène}$) 7,67 (2H, d, $J_{ortho}=8$, $H_{2,6}$) 8,69 (1H, m, $H_{thiophène}$) 10,05 (1H, se, OH).

b) SR 54047

The thiophene derivative obtained as per a) was condensed with 2-N,N-dimethylaminoethoxyamine hydrochloride as per Example 1c) previously described, yielding SR 45047, a mixture of 75% anti isomer and 25% syn isomer.

M.P.=170° C.

EXAMPLE 7

Trans 1-N,N-dimethylaminoethoxyimino 1-(2-thienyl) 3-(4-hydroxyphenyl) 2-propene: SR 45051

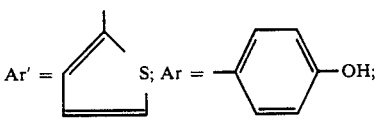

$M = H; n = 2; NR_1R_2 = N(CH_3)_2$ a) Preparation of trans 1-(2-thienyl) 3-(4-hydroxyphenyl) 2-propene 1-one 12.75 g of 2-acetyl thiophene and 12.10 g of 4-hydroxy benzaldehyde were dissolved in 20 ml water. Add a solution of 12.5 g NaOH in 12.5 ml water and agitate the reaction mixture at ambient temperature for 4 days.

Pour the reaction mixture into 300 ml of 10% hydrochloric acid, filter the precipitate, dissolve in 200 ml methanol, add vegetable carbon, filter over celite, concentrate the filtrate in vacuo, dissolve the residue in water, make alkaline at pH 11 and extract with ether.

Add hydrochloric acid until a precipitate forms, and filter. Chromatograph over silica gel, using hexane and ethyl acetate (70-30 v/v) as eluent. The fraction containing the expected product is concentrated in vacuo and the residue is recrystallized from methylene chloride.

M=2.43 g

NMR spectrum 6,79 (2H, d, $J_{ortho}=8$, $H_{3,5}$) 7,61 (2H, s, HC=CH); 7,68 (2H, d, $J_{ortho}=8$, $H_{2,6}$) 7,24; 7,96; 8,22 (3H, m, $H_{thiophène}$).

b) SR 45051

The thiophene derivative obtained as per a) was condensed with 2-N,N-diethylaminoethoxyamine as per Example 1c) described hereinbefore, yielding SR 45051, a mixture of 20% anti isomer and 80% syn isomer.

M.P.=140° C.

EXAMPLE 8

Trans 1-N,N-dimethylaminoethoxyimino 1-phenyl 3-(3-methoxy 4-hydroxyphenyl) 2-propene: SR 45744

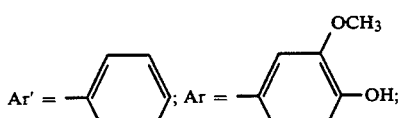

$-NR_1R_2 = -N(CH_3)_2; M = H; n = 2$

This compound was prepared as per Example 1. A mixture of 76% anti isomer and 24% syn isomer was obtained after recrystallization from ethanol.

M.P.=152° C.

EXAMPLE 9

Trans 1-N,N-dimethylaminoethoxyimino 1-(2-chlorophenyl) 3-(4-hydroxyphenyl) 2-propene syn.: SR 46220

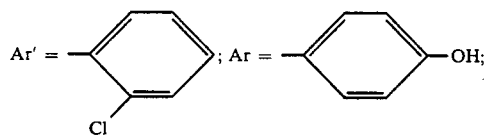

NR$_1$R$_2$ = N(CH$_3$)$_2$; M = H; n = 2

A) Preparation of the chalcone from 4-hydroxy benzaldehyde

2'-chloro 4-hydroxy chalcone 20 g of 2-chloro acetophenone and 15.8 g 4-hydroxy benzaldehyde were dissolved in 100 ml ethanol saturated with gaseous hydrochloric acid and the mixture was left at ambient temperature for 3 days. The ethanol was concentrated in vacuo. The residue was dissolved in 200 ml isopropanol, after which 500 ml water was added with agitation and the precipitate was filtered. The yield after recrystallization from isopropanol was 25.4 g of the expected chalcone.
M.P.=141° C.

B) Preparation of the chalcone from 4-methoxy benzaldehyde a) 2'-chloro 4-methoxy chalcone 30 g of 2-chloro acetophenone and 26.4 g 4-methoxy benzaldehyde were introduced into a mixture, cooled in ice, of 1.8 g soda pellets, 88 ml water and 55 ml 950 alcohol. The temperature was kept between 20° and 25° C. and the reaction mixture was agitated for 4 hours, then left at 5° C. for 10 hours. 150 ml of ice water were then added to the mixture and a precipitate was separated by filtration and then washed in water and in ethanol to obtain the expected chalcone.
m=50.6 g
M.P.=83° C.

b) 2'-chloro 4-hydroxy chalcone 30 g of chalcone obtained previously was dissolved in 150 ml dichloromethane. The solution was cooled to −70° C. after which 28.4 ml of boron tribromide were added. After the addition, the reaction mixture was agitated at ambient temperature for 2 hours, then poured on to 200 g of ice. The precipitate was filtered then recrystallized from ethanol.
m=17 g
M.P.=141° C.
SR 46220

4 g of 2'-chloro 4-hydroxy chalcone obtained previously and 4 g of 2-N,N-dimethylaminoethoxyamine dihydrochloride were dissolved in 100 ml ethanol and the reaction mixture was agitated at 40° C. for 72 hours.

The ethanol was concentrated in vacuo and the residue was dissolved in water and washed with ethanol. The aqueous phase was made alkaline with a solution of sodium bicarbonate and extracted with methylene chloride. After drying and filtration, the organic phase was concentrated in vacuo and the residue was dissolved in ether, yielding 3.25 g of SR 46620 containing 50% a and 50% s.

EXAMPLE 10

Preparation of the oxalate of SR 46220: SR 46220 A 0.53 g of SR 46620 and 0.138 g of oxalic acid were dissolved in 5 ml acetone. The mixture was agitated at ambient temperature for 1 hour then filtered, yielding 0.45 g of oxalate which was recrystallized from ethanol/ether, yielding 0.17 g of SR 46220 A (97% syn-3% anti).
M.P.=205° C.

EXAMPLE 11

Trans 1-N,N-dimethylaminoethoxyimino 1-(2-fluorophenyl) 3-(4-hydroxyphenyl) 2-propene syn: SR 46349

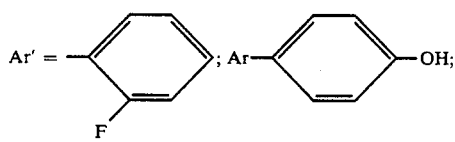

NR$_1$R$_2$ = N(CH$_3$)$_2$; M = H; n = 2

A) Preparation of the chalcone from 4-methoxy benzaldehyde a) 2'-fluoro 4-methoxy chalcone.

100 g of 2-fluoro acetophenone and 98.55 g of 4-methoxy benzaldehyde were dissolved in 360 ml of 2N ethanol hydrochloride then left at 5° C. for 6 days. 500 ml water was then added to the reaction mixture and the precipitate was filtered giving 120 g of the expected chalcone.
M.P.=55° C.

b) 2'-fluoro 4-hydroxy chalcone (SR 47035)

The procedure was as per Example 9 hereinbefore. The demethylated chalcone was obtained by action of boron tribromide.
M.P.=133° C. (isopropanol)

B) Preparation of the chalcone from 4-hydroxy benzaldehyde. SR 47035

100 g of 2-fluoro acetophenone and 88.4 g of 4-hydroxy benzaldehyde were dissolved in 2N ethanol hydrochloride, then left at 5° C. for 9 days. 1.2 liters of water was then added with agitation and the precipitaste was filtered, washed by trituration in water and filtered. The precipitate was dried then recrystallized from 2.5 liters of toluene, yielding 140.6 g of the expected chalcone.
M.P.=128° C.

C) SR 46349

85 g of the previously obtained chalcone and 85 g of 2-N,N-dimethylaminoethoxyamine dihydrochloride were dissolved in 1.5 l of 2N ethanol hydrochloride and reflux-heated for 5 hours. The mixture was concentrated in vacuo and the residue was dissolved in water, made alkaline with ammonia and fractionated as follows:
pH 5.8–6: 10.5 g anti (SR 46615 example n° 29)
pH 6–6.5: 84.9 g 45% a-55% s pH>7.5: 7 g syn. M.P.=162° C.: SR 46349

If made alkaline directly at pH>8, the base is obtained, comprising 44% syn and 55% anti.

NMR spectrum of SR 46349 2.00 (6H, s, N (CH₃)₂) 2,40 (2H, t, O CH₂ CH₂ N—) 4,05 (2H, t, O CH₂ CH₂ N—) 6,15 (1H, d, H—C=) 6,65 (2H, d, H₃,₅) 6,90 (1H, d, H—C=) 7,1 à 7,5(6H, m, H₃',₄',₅',₆' et H₂,₆) 9,70 (1H, s, ArOH)

Oximation of chalcone SR 47035 can alternatively be brought about using 2-N,N-dimethylaminoethoxyamine hydrochloride in ethanol in the presence of methanesulphonic acid or hydrochloric acid, to obtain the expected oxime.

EXAMPLE 12

Trans 1-N,N-dimethylaminoethoxyimino 1-(2-fluorophenyl) 3-(4-hydroxyphenyl) 2-propene hemifumarate syn. SR 46349 B.

A) Separation of the syn and anti isomers starting from SR 46349 (45% syn, 55% anti) by forming the hemifumarate.

A homogeneous mixture of 41.2 g of crystallized SR 46439 and 7.23 g of fumaric acid was prepared. 300 ml of 95° ethanol was then added with agitation at ambient temperature for 1½ hours. The mixture was then filtered, yielding 18 g of syn hemifumarate which was recrystallized from 95° ethanol at 60° C.

m=9 g
M.P.=190° C.

NMR spectrum 2,20 (6H, s, N (CH₃)₂) 2,68 (2H, t, O—CH₂ CH₂ N—) 4,20 (2H, t, O—CH₂ CH₂ N—) 6,25 (1H, d, H—C=) 6,53 (1H, s, fumarate) 6,75 (2H, d, H₃,₅) 6,95 (1H, d, H—C=) 7,2 à 7,6 (6H, m, H₃',₄',₅',₆' et H₂,₆) 9.6 to 12 (widened signal, —CO₂H+DOH 9.90 (1H, s, Ar-OH)

B) Isomerization of SR 46615 A (anti isomer of the hemifumarate of SR 46349).

45 g of anti hemifumarate of SR 46349 was dissolved in 500 ml 95° ethanol in the presence of 80 ml concentrated hydrochloric acid. The mixture was then reflux-heated for 6 hours, with exclusion of light, then concentrated in vacuo. The residue was dissolved in water and washed with ether. The aqueous phase was then made alkaline with ammonia and a precipitate was separated by filtration.

The yield was 35.7 g of base (45% syn+55% anti), which was treated as before, yielding SR 46349 B.

EXAMPLE 13

Trans 1-N,N-dimethylaminoethoxyimino 1-(2-methoxyphenyl) 3-(4-hydroxyphenyl) 2-propene oxalate, syn: SR 46023 A.

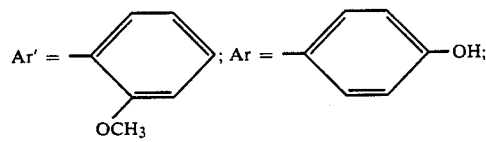

$NR_1R_2 = N-(CH_3)_2$; M = H; n = 2

2.6 g of oxalic acid was added to a suspension of 10 g of 1-N,N-dimethylaminoethoxyimino 1-(2-methoxyphenyl) 3-(4-hydroxyphenyl) 2-propene (SR 45743, 54% anti+46% syn) in 200 ml actone, and agitated for an hour. The oxalate was then filtered and agitated in 10 ml ethanol and then filtered, yielding 1.9 g of syn oxalate. M.P.=192° C.

NMR spectrum 2,60 (6H, s, N (CH₃)₂) 3,25 (2H, t, O—CH₂ CH₂ N—) 3,70 (3H, s, Ar'—O CH₃) 4,30 (2H, t, O—CH₂ CH₂ N—) 6,20 (1H, d, H—C=) 6,70 (2H, d, H₃,₅) 6,90 (1H, d, H—C=) 6,95 à 7,5 (6H, m, H₃',₄',₅',₆' and H₂,₆) 9,80 (1H, s, Ar—OH) 7 à 9,5 (se, H oxalate+DOH)

The products according to the invention, synthesized under experimental conditions similar to those in Examples 1 to 13, are listed in Tables 1, 2 and 3 hereinafter.

The following abbreviations have been used in the Tables to denote the recrystallization solvents:
EtOH: ethanol
iPrOH: isopropyl alcohol
DMF: dimethylformamide
AcOEt: ethyl acetate
CH₃CN: acetonitrile
Tert-BuOH: tertiobutanol
BuOH: butanol

TABLE 1

Examples 14 to 55

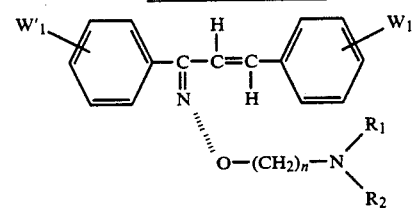

| Product n° SR Examples n° | W'₁ | W₁ | n | —N(R₁)(R₂) | Salt or base | Isomer % a-% s | F, °C. Solvent recryst. |
|---|---|---|---|---|---|---|---|
| 40258 A 14 | H | H | 2 | N—(CH₃)₂ | oxalate acid | a | 170 acétone |
| 45048 A 15 | H | H | 2 | N—(CH₃)₂ | hémi oxalate | s | 180 acétone |
| 45560 A 16 | H | H | 3 | N—(CH₃)₂ | oxalate acid | 65a-35s | 160 EtOH |
| 45071 17 | H | 2-OH | 2 | N—(CH₃)₂ | base | a | 159 AcOEt |
| 40613 18 | H | 3-OH | 2 | N—(CH₃)₂ | fumarate | a | 140-2 EtOH |

TABLE 1-continued

Examples 14 to 55

(I)

| Product n° SR Examples n° | W'$_1$ | W$_1$ | n | $-N\begin{matrix}R_1\\R_2\end{matrix}$ | Salt or base | Isomer % a-% s | F, °C. Solvent recryst. |
|---|---|---|---|---|---|---|---|
| 45172 19 | H | 4-OH | 3 | N—(CH$_3$)$_2$ | base | 92a–8s | 143 AcOEt |
| 45287 20 | H | 4-OH | 2 | piperidinyl | base | 75a–25s | 181 i-PrOH |
| 45288 21 | H | 4-OH | 2 | morpholinyl | base | 85a–15s | 126 i-PrOH |
| 45289 A 22 | H | 4-OH | 3 | piperazinyl-NH | fumarate | 90a–10s | 218 EtOH |
| 46349 A 23 | 2-F | 4-OH | 2 | N—(CH$_3$)$_2$ | oxalate | 40a–60s | * |
| 46349 C 24 | 2-F | 4-OH | 2 | N—(CH$_3$)$_2$ | méthane sulfonate | s | 142 tert-BuOH |
| 46349 D 25 | 2-F | 4-OH | 2 | N—(CH$_3$)$_2$ | hémi-sulfate | s | 130–145 H2O |
| 46349 E 26 | 2-F | 4-OH | 2 | N—(CH$_3$)$_2$ | phosphate | s | 130–150 H2O |
| 46349 F 27 | 2-F | 4-OH | 2 | N—(CH$_3$)$_2$ | maléate acide | s | 140 H2O |
| 46349 G 28 | 2-F | 4-OH | 2 | N—(CH$_3$)$_2$ | Hydrochloride | s | * |
| 46615 A 29 | 2-F | 4-OH | 2 | N—(CH$_3$)$_2$ | hémi-fumarate | a | * |
| 46564 A 30 | 2-F | 4-OCH$_3$ | 2 | N—(CH$_3$)$_2$ | oxalate | 20a–80s | * |
| 46220 B 31 | 2-Cl | 4-OH | 2 | N—(CH$_3$)$_2$ | hémi-fumarate | s | 198–200 EtOH |
| 46251 A 32 | 2-Cl | 4-OCH$_3$ | 2 | N—(CH$_3$)$_2$ | oxalate | 30a–70s | 118–123 CH$_2$Cl$_2$/ether |
| 46110 A 33 | 2-Cl | 4-OCH$_3$ | 3 | N—(CH$_3$)$_2$ | oxalate | 40a–60s | 127 acétone |
| 46190 A 34 | 2-Cl | 4-OCH$_3$ | 3 | N—(CH$_3$)$_2$ | oxalate | s | 147 BuOH/éther |
| 46278 A 35 | 2-Br | 4-OCH$_3$ | 2 | N—(CH$_3$)$_2$ | oxalate | 30a–70s | * |
| 46217 A 36 | 2-CH$_3$ | 4-OCH$_3$ | 2 | N—(CH$_3$)$_2$ | oxalate | 15a–85s | 96 i-PrOH |
| 45743 A 37 | 2-OCH$_3$ | 4-OCH$_3$ | 2 | N—(CH$_3$)$_2$ | base | 54a–46s | 158 EtOH |
| 46057 38 | 2-OCH$_3$ | 4-OH | 3 | N—(CH$_3$)$_2$ | base | 80a–20s | 158 EtOH/H2O |
| 46057 A 39 | 2-OCH$_3$ | 4-OH | 3 | N—(CH$_3$)$_2$ | oxalate | a | 151 EtOH/éther |
| 46109 40 | 2-OCH$_3$ | 4-OH | 3 | N—(CH$_3$)$_2$ | base | 10a–90s | 129 EtOH |
| 46289 A 41 | 2-OCH$_3$ | 4-OH | 3 | N—(CH$_3$)$_2$ | base | 52a–48s | * |
| 46219 A 42 | 2-OCH$_3$ | 4-OCH$_3$ | 3 | N—(CH$_3$)$_2$ | oxalate | a | 147 CH$_2$Cl$_2$ |
| 46165 A 43 | 2-OCH$_3$ | 4-OCH$_3$ | 2 | N—(CH$_3$)$_2$ | oxalate | 30a–70s | 146 i-PrOH |
| 46175 44 | 2-NO$_2$ | 4-OH | 2 | N—(CH$_3$)$_2$ | base | s | 127–135 CH$_2$Cl$_2$/éther |

TABLE 1-continued
Examples 14 to 55

[Structure I: diaryl imine with O-(CH2)n-NR1R2 substituent]

| Product n° SR Examples n° | W'1 | W1 | n | -N(R1)(R2) | Salt or base | Isomer % a-% s | F, °C. Solvent recryst. |
|---|---|---|---|---|---|---|---|
| 46400 44 | 2-CF3 | 4-OH | 2 | N—(CH3)2 | base | 50a-50s | * |
| 45678 45 | 2-NO2 | 4-OH | 2 | N—(CH3)2 | base | 93a-7s | 180 CH3CN |
| 45573 46 | 4-F | 4-OH | 2 | N—(CH3)2 | base | 75a-25s | 188 EtOH |
| 45174 A 47 | 4-Cl | 4-OH | 2 | N—(CH3)2 | Hydrochloride | a | 218 EtOH |
| 45574 A 48 | 4-I | 4-OH | 2 | N—(CH3)2 | hémi oxalate | s | 219 DMF |
| 45290 49 | 4-I | 4-OH | 2 | N—(CH3)2 | base | a | 183 AcOEt |
| 45291 50 | 4-OH | 4-OH |  | N—(CH3)2 | base | 75a-25s | 265 DMF/EtOH |
| 45681 A 51 | H | 4-N—(CH3)2 | 2 | N—(CH3)2 | Hydrochloride | 20a-80s | 218 CH3CN/ Ethyl ether |
| 45682 A 52 | H | 4-N—(CH3)2 | 2 | N—(CH3)2 | oxalate | 70a-30s | 162 CH3CN |
| 46216 A 53 | H | 4-OCO—C2H5 | 2 | N—(CH3)2 | oxalate | s | 150 acétone |
| 46025 A 54 | H | 4-OCH2—CO2H | 2 | N—(CH3)2 | Hydrochloride | 60a-40s | — éther |

TABLE 2
Examples 56 to 63

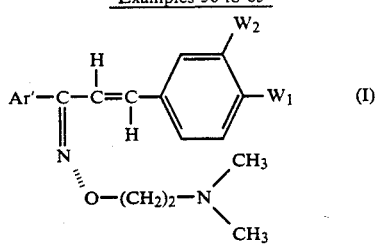

| Product n° Sr Example No. | Ar | W1 | W2 | Salt or base | Isomer % a-% s | F, °C. Solvent recryst. |
|---|---|---|---|---|---|---|
| 45099 A 56 | thienyl (S) | OH | H | hémi fumarate | anti | 160 i-PrOH |
| 45100 A 57 | thienyl (S) | OH | H | fumarate | syn | 147 acétone |

TABLE 2-continued
Examples 56 to 63
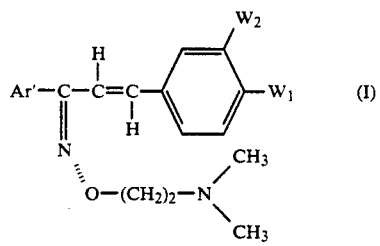
| Product n° Sr Example No. | Ar | W1 | W2 | Salt or base | Isomer % a-% s | F, °C. Solvent recrystal. |
|---|---|---|---|---|---|---|
| 45097 58 | 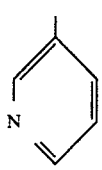 | OH | H | base | 80a–20s | 130 CH₃CN |
| 45052 59 | 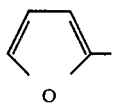 | OH | H | base | 80a–20s | 139 AcOEt |
| 46218 A 60 | 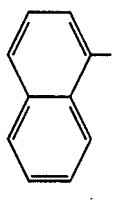 | OCH₃ | H | oxalate | 43a–57s | * |
| 46252 A 61 | 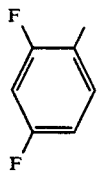 | OCH₃ | H | oxalate | s | 156–164 EtOH/éther |
| 46039 62 | 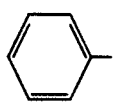 | OH | OH | base | 84a–16s | 180 CH₃CN |
| 46134 63 | 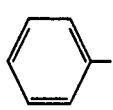 | OCH₃ | OCH₃ | base | 22a–78s | 55–56 EtOH |

TABLE 3

Examples 64 to 66

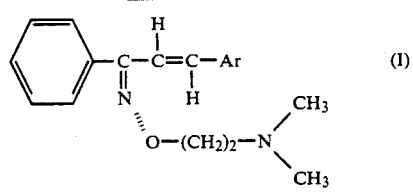

| Product n° SR Example n° | Ar | Salt or base | Isomer % a–% s | F, °C. | Solvent recryst. |
|---|---|---|---|---|---|
| 45745 64 | 9-anthracenyl | Hydrochloride | 48a–52s | 178 | i-PrOH |
| 45746 65 | 2-anthracenyl | Hydrochloride | a | 204 | EtOH |
| 45558 A 66 | 4-pyridyl | maléate | 90a–10s | 144 | i-PrOH |

EXAMPLE 67

Trans 1-(2-aminoethoxyimino) 1-phenyl 3-(4-hydroxyphenyl) 2-propene acid oxalate: SR 45683 A.

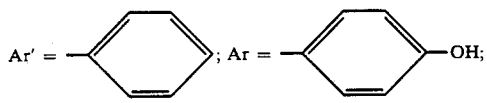

$NR_1R_2 = NH_2$; $M = H$; $n = 2$ a) Trans 1-(2-bromoethoxyimino) 1-phenyl 3-(4-hydroxyphenyl) 2-propene 20 g of 4-hydroxy chalcone and 20 g of 1-oxyamino 2-bromoethane hydrobromide were mixed in solution in 200 ml absolute ethanol. Agitate the reaction mixture at ambient temperature overnight, concentrate the ethanol in vacuo, dissolve the residue in ethyl alcohol, filter the precipitate and rinse it in ethyl ether.

1M = 33.7 g b) SR 45683 A 1 g of the product obtained in a) hereinbefore was dissolved in 10 ml ethanol saturated with ammonia.

The solution was left at ambient temperature for 10 days, and the ethanol was concentrated in vacuo. Dissolve residue in water, make alkaline with sodium bicarbonate, extract with ethyl acetate, dry over magnesium sulphate, filter and concentrate in vacuo. The residue was dissolved when hot in 15 ml acetone, and 250 mg oxalic acid was added. The solution was allowed to return to ambient temperature and the crystals were filtered, rinsed in acetone and recrystallized from ethanol, giving 180 mg of the anti isomer.

M.P. = 210° C.

EXAMPLE 68

Trans 1-N,N-diisopropylaminoethoxyimino 1-phenyl 3-(4-hydroxyphenyl) 2-propene hydrochloride: SR 45680 A

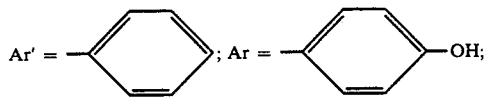

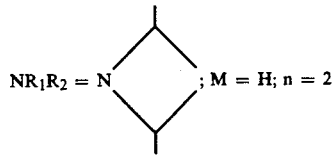

$NR_1R_2 = $ (diisopropylamino); $M = H$; $n = 2$ 2 g of the product obtained as per Example 67a) hereinbefore was dissolved in 10 ml dimethyl formamide. Add 10 ml diisopropylamine and heat the reaction mixture at 70° C. for 24 hours, concentrate in vacuo, dissolve residue in water, dry over magnesium sulphate and concentrate in vacuo.

Chromatograph the residue on silca gel, using 90–10 (v.v.) methylene chloride and methanol as eluent. The fractions of pure product were concentrated in vacuo. The residue was dissolved in ether, ether hydrochloride was added and the hydrochloride was precipitated and recrystallized from acetonitrile, yielding 270 mg of the anti isomer.

M.P.=188° C.

EXAMPLE 69

Trans 1-N-methylaminoethoxyimino 1-(2-fluorophenyl) 3-(4-hydroxyphenyl) 2-propene. SR 46616 A.

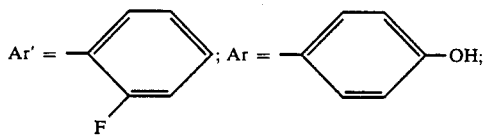

$NR_1R_2 = NH-CH_3$; $M = H$; $n = 2$ a) 2-bromo N-ethoxycarbonyl N-methylethylamine dihydrobromide 197 ml of 30% soda was added to 540 ml water followed by 313 g of 2-bromo N-methyl ethylamine hydrobromide. The mixture was cooled to 10° C. and 155 ml of ethyl chlorofomate was added, keeping the temperature below 15° C. After agitation overnight at ambient temperature, the aqueous phase was decanted, extracted with ether, washed twice in water and dried over magnesium sulphate, yielding 142 g of the expected product.

b) N-(N-ethoxycarbonyl 2-N-methylaminoethoxy) phthalimide

The aforementioned derivative was added to a mixture of 108 g N-hydroxy phthalimide and 92.5 ml triethylamine in 100 ml DMF and heated at 87° C. for 3 days. The DMF was evaporated and the mixture was extracted with dichloromethane and washed with a solution of sodium carbonate and then with water. It was dried over magnesium sulphate and evaporated in vacuo. The residue was redissolved in methanol and crystallized by adding water, obtaining 100 g of the expected product.

c) 2-N-methylaminoethoxyamine hydrobromide

A solution of 100 g of the aforementioned product was reflux-heated for an hour in a mixture of 366 mg HBr 46% and 246 ml acetic acid. The mixture was cooled to 5°, the insoluble substance was filtered, and the filtrate was evaporated in vacuo. The residue was triturated hot in tertiobutanol, yielding 22.1 g of the expected product.

d) SR 46616 A.

A mixture of 4 g 2'-fluoro 4-hydroxy chalcone and 8.1 g hydroxylamine as hereinbefore was reflux-heated for 1½ hours in 100 ml ethanol, then evaporated to dryness in vacuo. The residue was treated with water, extracted twice with ether, made alkaline with sodium bicarbonate, and extracted with chloroform. The chloroform phase was washed with a solution of sodium bicarbonate, dried over $MgSO_4$ and evaporated, yielding 2.3 g of syn-anti mixture.

Hemifumarate

A mixture of 1.63 g of the aforementioned base and 300 mg of fumaric acid in ethanol was agitated for 30 minutes and left overnight at −15° C. 1.45 g of anti isomer was filtered. The filtrate was concentrated, yielding 140 mg of SR46616A (a mixture of 70% syn and 30% anti).

The compounds listed in Table 4 were synthesized as per Examples 67, 68 and 69.

TABLE 4

Examples 70 to 81

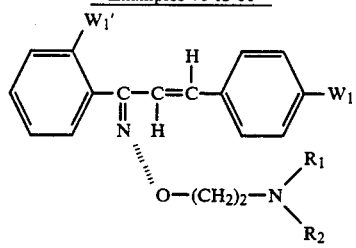

| Product n° SR Example | $W_1'$ | $W_1$ | $-N\begin{smallmatrix}R_1\\R_2\end{smallmatrix}$ | Salt or base | Isomer % a-% s | F, °C. Solvent recrystal. |
|---|---|---|---|---|---|---|
| 45997 A 70 | H | OH | $NH-CH_3$ | base | 43a-57s | 160 $CH_3CN$ |
| 45998 A 71 | H | OH | $NH-CH_3$ | base | a | 122 éther |
| 46133 72 | H | OH | $NH-CH_3$ | oxalate | 10s-90s | * |
| 46386 A 73 | Cl | OH | $NH_2$ | oxalate | a | * |
| 46385 A 74 | Cl | OH | $NH_2$ | oxalate | 55a-45s | * |
| 46384 A 75 | Cl | OH | $NH-CH_3$ | oxalate | 50a-50s | * |
| 46387 A 76 | $OCH_3$ | OH | $NH_2$ | oxalate | 90a-10s | * |
| 46336 A 77 | $OCH_3$ | OH | $NH-CH_3$ | oxalate | 77a-23s | * |
| 46563 A 78 | $OCH_3$ | OH | $NH-CH_3$ | hémifumarate | 50a-50s | * |
| 46279 79 | $OCH_3$ | OH | $N-(C_2H_5)_2$ | base | 80a-20s | * |

TABLE 4-continued

Examples 70 to 81

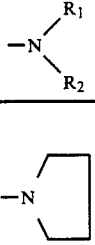

| Product n° SR Example | $W_1'$ | $W_1$ | $-N\diagdown{R_1 \atop R_2}$ | Salt or base | Isomer % a-% s | F, °C. Solvent recrystal. |
|---|---|---|---|---|---|---|
| 46132 80 | OCH$_3$ | OH | 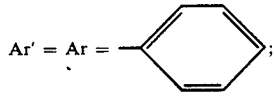 | base | 46a–54s | * |
| 46401 81 | OCH$_3$ | OH | $\underset{\underset{N-(CH_2)_2-OH}{\mid}}{H}$ | base | 73a–27s | * |

EXAMPLE 82

Trans 1-N,N-dimethylaminoethoxyimino 1,3-diphenyl 2-propene hydrochloride: CM 40258

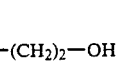

$NR_1R_2 = N(CH_3)_2$; M = H; n = 2

A mixture of 5.1 g of the oxime of benzalacetophenone, 1.3 g of sodium hydride in suspension in oil (55–60%) and 25 ml dimethylformamide was agitated at 20° C. for an hour.

Then add 1.2 g sodium hydride in suspension in oil (55–60 %) at 10; followed by 4 g of 2-dimethylamino 1-chloroethane hydrochloride, and agitate the reaction mixture at 20° C. for 20 hours.

Pour the reaction mixture into 100 ml water, extract with ether, acidify with a solution of hydrochloric acid, decant the aqueous phase, make alkaline with potassium carbonate, and decant 6.3 g of an oil which is reacted with a solution of hydrochloric acid in ethyl ether. Recrystallize the hydrochloride from acetone.

M = 4.8 g
M.P. = 209°–210° C.

EXAMPLE 83

Trans 2-chloro 1-N,N-dimethylaminoethoxyimino 1-phenyl 3-(4-methoxyphenyl) 2-propene oxalate, syn. SR 46356 A.

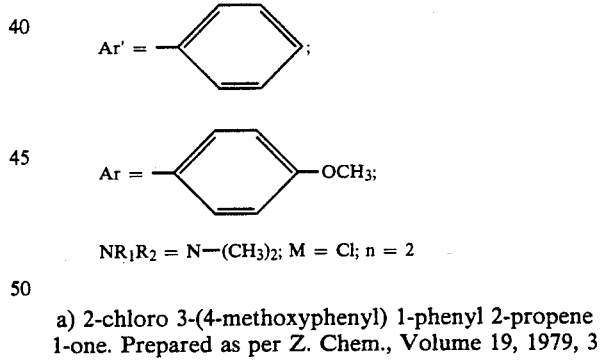

$NR_1R_2 = N-(CH_3)_2$; M = Cl; n = 2 a) 2-chloro 3-(4-methoxyphenyl) 1-phenyl 2-propene 1-one. Prepared as per Z. Chem., Volume 19, 1979, 3 b) SR 46356 A 1.4 g of the product obtained as in a) and 2 g of 2-N,N-dimethylaminoethoxyamine dihydrochloride were dissolved in 40 ml absolute ethanol and the reaction mixture was reflux-heated for 24 hours. The ethanol was concentrated in vacuo, the residue was dissolved in water and washed in ether, and the aqueous phase was made alkaline with sodium bicarbonate, extracted with dichloromethane, dried and concentrated in vacuo. The resulting oil was dissolved in 30 ml acetone, after which 1.5 g of oxalic acid was added. The oxalate was filtered and recrystallized from ethanol, yielding 2.1 g of SR 46356 A.

The compounds listed in Table 5 were prepared as per Example 83.

TABLE 5

Examples 84 to 88

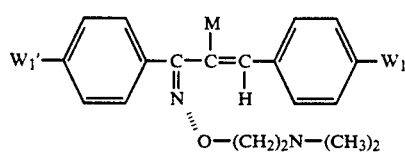

| Product n° SR Example n° | W₁' | W₁ | M | Salt or base | Isomer % a-% s | F, °C. Solvent recryst. |
|---|---|---|---|---|---|---|
| 46351 A 84 | H | OCH₃ | Cl | oxalate | 80a-20s | * |
| 46348 A 85 | H | OCH₃ | Br | oxalate | s | 172-180 EtOH-ether |
| 46254 A 86 | H | OH | —(CH₂)₂—CH₃ | oxalate | 80a-20s | 137-147 CH₂Cl₂/éther |
| 46253 A 87 | H | OH | —(CH₂)₂—CH₃ | oxalate | 30a-70s | 189-193 acétone |
| 46163 A 88 | Cl | OH | —CH₂—CH₃ | Hydrochloride | s | 213 EtOH |

TABLE 6

NMR-Main chemical shifts

| Example No | —N—(CH₃)n | —N—CH₂— | —O—CH₂— | —OCH₃ |
|---|---|---|---|---|
| 23 | 2,20 | 2,68 | 4,20 | — |
| 28 | 2,65 | 3,35 | 4,45 | — |
| 29 | 2,35 | 2,80 | 4,30 | — |
| 30 | 2,60 2,80 | 3,25 3,40 | 4,40 4,50 | 3,75 |
| 35 | 2,60 2,80 | 3,30 3,40 | 4,40 4,50 | 3,75 |
| 41 | 2,10 2,15 | 2,15 2,30 | 4,00 4,10 | 3,70 |
| 45 | 2,00 2,20 | 2,40 2,55 | 4,05 4,20 | — |
| 60 | 2,45 2,85 | 3,20 3,45 | 4,30 4,50 | 3,70 |
| 72 | 2,50 2,55 | 3,20 | 4,20 | — |
| 73 | — | 3,05 | 4,20 | — |
| 74 | — | 2,85 3,05 | 4,10 4,25 | — |
| 75 | 2,50 2,65 | 3,15 3,30 | 4,25 4,35 | — |
| 76 | — | 3,20 | 4,25 | 3,70 |
| 77 | 2,65 | 3,25 | 4,30 | 3,70 |
| 78 | 2,35 2,50 | 2,85 3,10 | 4,10 4,25 | 3,70 |
| 79 | — | 2,40 2,55 | 4,00 4,15 | 3,70 |
| 80 | — | 2,35 2,50 2,60 2,70 | 4,10 4,20 | 3,70 |
| 81 | — | 2,50 2,60 2,70 2,80 | 4,00 4,10 | 3,70 |
| 84 | 2,65 2,70 | 3,30 3,40 | 4,40 4,50 | 3,80 |

We claim:

1. Propenone oxime ethers having the trans geometry with respect to the double ethylene bond and having the formula:

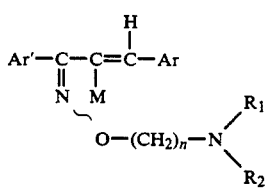

(I)

in which

Ar and Ar' can each independently denote either:
(a) a phenyl group, non-substituted or mono or polysubstituted by a halogen atom, a lower alkyl grouping (containing 1 to 4 carbon atoms), a nitro, hydroxyl, alkoxy (1-4 carbon atoms), acyloxy (1-4 carbon atoms), dimethylamino or carboxyalkoxy grouping in which the alkylene contains 1-4 carbon atoms; or a 9-anthryl group or a naphthyl group, or (b) a heteroaromatic group selected from the group consisting of pyridyl, thienyl and furyl groups;

$R_1$ and $R_2$ each independently denote a hydrogen atom or a lower alkyl grouping (1-4 carbon atoms) or $R_1$ and $R_2$ together with the nitrogen atom to which they are bonded constitute 1-pyrrolidinyl or piperidino or morpholino or 1-piperazinyl grouping;

M represents a hydrogen atom or a chlorine or bromine atom, or a straight or branched lower alkyl containing 1-6 carbon atoms, and n=2 or 3, and pharmaceutically acceptable acid addition salts of said propenone oxime ethers.

2. A propenone oxime ether according to claim 1, having the formula:

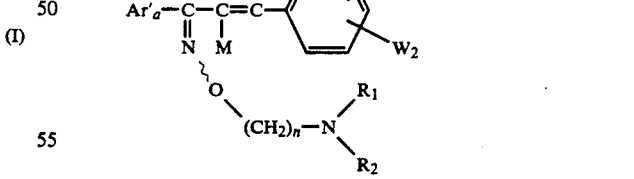

(Ib)

where $Ar'_a$ represents a group chosen from among pyridyl, thienyl, furyl or 9-anthryl and $W_1$ and $W_2$ each independently represent a hydrogen atom or a halogen atom or a lower alkyl grouping (1-4 carbon atoms) or a nitro or hydroxyl or alkoxy (1-4 carbon atoms) or acyloxy (1-4 carbon atoms) or dimethyl amino or carboxyalkoxy grouping in which the alkylene contains 1 to 4 carbon atoms, or a pharmaceutically acceptable acid addition salt of said propenone oxime ethers.

3. A propenone oxime ether according to claim 1, having the formula:

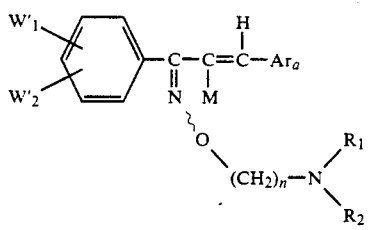

(Ic)

in which $Ar_a$ represents a group chosen from among pyridyl, thienyl, furyl or 9-anthryl and $W'_1$ and $W'_2$ each independently represent a hydrogen atom or a halogen atom or a lower alkyl grouping (1 to 4 carbon atoms) or a nitro, hydroxyl, alkoxyl (1 to 4 carbon atoms), acyloxy (1 to 4 carbon atoms), dimethylamino or carboxyalkoxy group in which the alkylene contains 1 to 4 carbon atoms, or a pharmaceutically acceptable acid addition salt of said propenone oxime ethers.

4. A propenone oxime ether according to claim 1, having the formula:

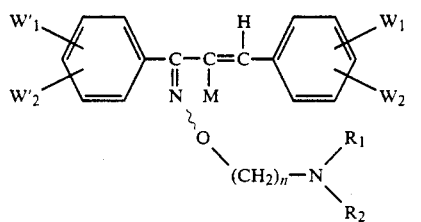

(Id)

in which $W_1$, $W_2$, $W'_1$, $W'_2$ can each independently denote a hydrogen atom, or a halogen atom or a lower alkyl grouping (1-4 carbon atoms) or a nitro or hydroxyl or alkoxyl (1-4 carbon atoms) or acyloxy (1-4 carbon atoms) or dimethylamino or carboxyalkoxy grouping in which the alkylene contains 1 to 4 carbon atoms, or a pharmaceutically acceptable acid addition salt of said propenone oxime ethers.

5. A propenone oxime ether according to claim 1, having the formula:

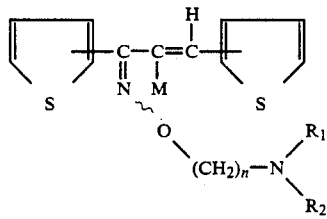

(Ie)

in which the substituents are a 2-thienyl or a 3-thienyl or a pharmaceutically acceptable acid addition salt of said propenone oxime ethers.

6. A propenone oxime ether according to claim 1, which is trans 1-N,N-dimethylaminoethoxyimino 1-(2-fluorphenyl) 3-(4-hydroxyphenyl) 2-propene syn or a pharmaceutically acceptable acid addition salt thereof.

7. A propenone oxime ether according to claim 1, which is trans 1-N,N-dimethylaminoethoxyimino 1-(2-fluorophenyl) 3-(4-hydroxyphenyl) 2-propene syn methanesulphonate.

8. A propenone oxime ether according to claim 1, which is trans 1-N,N-dimethylaminoethoxyimino 1-(2-fluorophenyl) 3-(4-hydroxyphenyl) 2-propene syn hemifumarate.

9. Trans 1-N,N-dimethylaminoethoxyimino 1-(2-methoxyphenyl) 3-(4-hydroxyphenyl) 2-propene syn or a pharmaceutically acceptable acid addition salt thereof.

10. Trans 1-N,N-dimethylaminoethoxyimino 1-(2-chlorophenyl) 3-(4-hydroxyphenyl) 2-propene syn or a pharmaceutically acceptable acid addition salt thereof.

11. A pharmaceutical composition in which the active principle is a compound according claim 1 with a pharmaceutically acceptable carrier.

12. A pharmaceutical composition according to claim 11 and in the form of a dose unit, in which the active principle is mixed with a pharmaceutical excipient.

13. A pharmaceutical composition according to claim 11 and containing 0.1 to 500 mg of active principle per unit dose with a pharmaceutically acceptable carrier.

14. A pharmaceutical composition according to claim 11 containing 2.5 to 125 mg of active principle per unit dose with a pharmaceutically acceptable carrier.

15. Propenone oxime ethers having the trans geometry with respect to the double ethylene bond and having the formula:

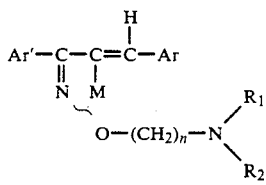

(I)

in which
Ar and Ar' can each independently denote either:
(a) a phenyl group, non-substituted or mono or polysubstituted by a halogen atom, a lower alkyl grouping (containing 1 to 4 carbon atoms), a nitro, hydroxyl, alkoxy (1-4 carbon atoms), acyloxy (1-4 carbon atoms), dimethylamino or carboxyalkoxy grouping in which the alkylene contains 1-4 carbon atoms; or a 9-anthryl group or a naphthyl group, or
(b) a heteroaromatic group selected from the group consisting of pyridyl, thienyl and furyl groups;

$R_1$ and $R_2$ each independently denote a hydrogen atom or a lower alkyl grouping (1-4 carbon atoms) or $R_1$ and $R_2$ together with the nitrogen atom to which they are bonded constitute a 1-pyrrolidinyl or piperidino or morpholino or 1-piperazinyl grouping;

M represents a hydrogen atom or a chlorine or bromine atom, or a straight or branched lower alkyl containing 1-6 carbon atoms, and n=2 or 3, and their mineral or organic acid addition salts, wherein the acid addition salts are selected from the group consisting of hydrochloride, hydrobromide, sulphate, hydrogen sulphate, dihydrogen phosphate, methane sulphonate, methyl sulphate, maleate, fumarate, naphthalene sulphonate and isethionate.

* * * * *